United States Patent [19]

Suda et al.

[11] Patent Number: 5,788,634

[45] Date of Patent: Aug. 4, 1998

[54] MULTI PURPOSE SENSOR

[75] Inventors: Shin Suda; Yoshihiro Sugo, both of Tokyo, Japan

[73] Assignee: Nihon Kohden Corporation, Tokyo, Japan

[21] Appl. No.: 871,768

[22] Filed: Jun. 9, 1997

Related U.S. Application Data

[63] Continuation of Ser. No. 351,535, Dec. 7, 1994, abandoned.

[30] Foreign Application Priority Data

Dec. 7, 1993 [JP] Japan ................... 5-065275 U

[51] Int. Cl.[6] ........................................ A61B 5/02
[52] U.S. Cl. ............... 600/382; 600/372; 600/513; 600/384; 600/386; 600/476; 600/480; 600/485; 600/504
[58] Field of Search ............... 600/372, 382, 600/384, 386, 476, 480, 494, 485, 504, 513, 324, 340, 344, 383, 500, 502, 473

[56] References Cited

U.S. PATENT DOCUMENTS

| 3,229,685 | 1/1966 | Ringkamp et al. | 128/667 |
| 4,539,997 | 9/1985 | Wesseling et al. | 128/667 |
| 5,372,136 | 12/1994 | Steuer et al. | 128/665 |
| 5,511,546 | 4/1996 | Hon | 128/667 |

Primary Examiner—Lee S. Cohen
Assistant Examiner—Stephen Huang
Attorney, Agent, or Firm—Sughrue, Mion, Zinn, Macpeak & Seas, PLLC

[57] ABSTRACT

The multi-purpose sensor includes a pair of arms, light-emitting device and light-receiving device that are fitted in an end portion of the arms, respectively, and electrodes that are made of an electrically conductive elastic material and which are bonded to end portion of the arms, respectively.

5 Claims, 2 Drawing Sheets

MULTI PURPOSE SENSOR

This is a Continuation of Application No. 08/351,535 filed Dec. 7, 1994 now abandoned.

BACKGROUND OF THE INVENTION

1. Field of the Invention

The present invention relates to a multi-purpose sensor that is an integral assembly of a pulse wave detecting sensor and electrocardiogram detecting electrodes and which is to be used in measuring the velocity of pulse wave propagation through the human body for various purposes such as the measurement of blood pressure and the degree of arteriosclerosis.

2. Related Art

Non-invasive blood pressure monitors are available in various types including a monitor for measuring blood pressure by detecting the velocity of pulse wave propagation and a device for measuring the degree of arteriosclerosis. When measuring blood pressure by this method, a pulse wave detecting sensor having a light-emitting device and a light-receiving device is attached to a peripheral part of a subject, such as a finger, an ear, the back of a hand or the instep of a foot and, at the same time, at least two electrodes for electrocardiogram detection have to be attached to specified sites of the subject's body. When the first R wave appears on an electrocardiogram, the delay time until the bottom value of pulse wave appears at a peripheral end of the subject such as a finger or an ear is detected as the velocity of pulse wave propagation for blood pressure measurement. The velocity of pulse wave propagation is expressed as a function of the modulus of volume elasticity of an arterial blood vessel, which increases with increasing blood pressure. This is the principle of determining blood pressure variations from changes in the velocity of pulse wave propagation.

The modulus of volume elasticity of an arterial blood vessel also changes due to arteriosclerosis and by the same mechanism as just described above, the degree of arteriosclerosis can be measured in terms of the time of pulse wave propagation at a given blood pressure.

The measurement of blood pressure or the degree of arteriosclerosis by the method described above has involved two major problems. First, the need to attach not only the pulse wave detecting sensor but also at least two electrodes for electrocardiogram detection on the body of a subject causes discomfort and cumbersomeness to the subject. Second, if strong pressure is exerted by the pulse wave sensor that is attached on a peripheral site of the subject such as a finger or an ear, the blood flow at that site is impeded; on the other hand, the sensor is prone to accidental disengagement if the attachment pressure is insufficient.

SUMMARY OF THE INVENTION

The present invention has been accomplished under these circumstances and has as an object providing a multi-purpose sensor for use in the measurement of at least blood pressure and the degree of arteriosclerosis that uses a smaller number of sensing elements to reduce the manufacturing cost while ensuring against any discomfort to the subject and which yet is capable of preventing accidental disengagement of the sensor without impeding the blood flow in the subject.

This object of the invention can be attained by the multi-purpose sensor for use in the measurement of the velocity of pulse wave propagation, which sensor comprises a pair of holding members for holding a human body part of interest, a light-emitting and a light-receiving device combination for pulse wave detection and electrodes for electrocardiogram detection, characterized in that said light-emitting device and said light-receiving device are provided in a face-to-face relationship in an end portion of said holding members and that at least one of said electrodes is provided in an end portion of either of said holding members.

According to the present invention, the multi-purpose sensor the electrodes are made of an electrically conductive elastic material.

According to the invention, at least one of the electrodes for electrocardiogram detection that are conventionally held to be necessary is made integral with the sensing element for pulse wave detection and this effectively reduces the number of sensing elements that have to be attached on the subject. Consequently, the manufacturing cost of the sensor is reduced and, at the same time, the sensor can be attached or detached in a sufficiently easy manner to alleviate the discomfort to the subject.

According to the present invention, the electrodes provided on the holding members are made of an electrically conductive elastic material and this insures that the holding members, as attached on a peripheral site of the subject's body, are kept compressed at a given pressure throughout the period of measurement, thereby effectively preventing accidental disengagement of the sensor without impeding blood flow.

DETAILED DESCRIPTION OF THE PREFERRED EMBODIMENTS

A multi-purpose sensor according to an embodiment of the invention will now be described with reference to the accompanying drawings.

Figure 1:
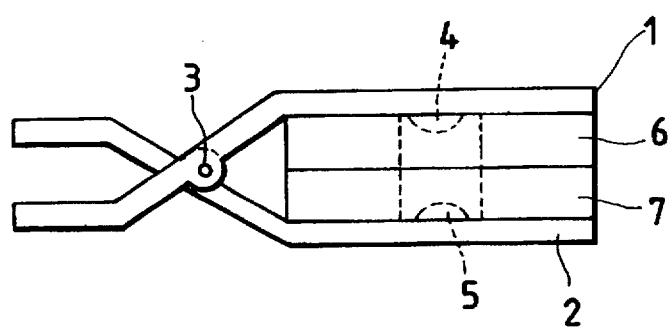
FIG. 1 is a side view showing the construction of a multi-purpose sensor according to an embodiment of the invention.
Figure 2:
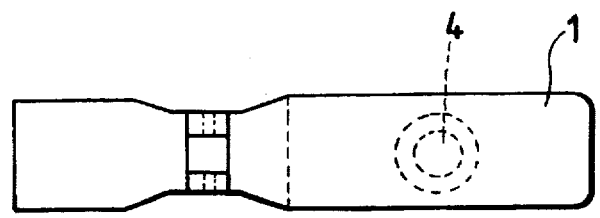
FIG. 2 is a plan view showing the construction of the first arm s own in FIG. 1.
Figure 3:
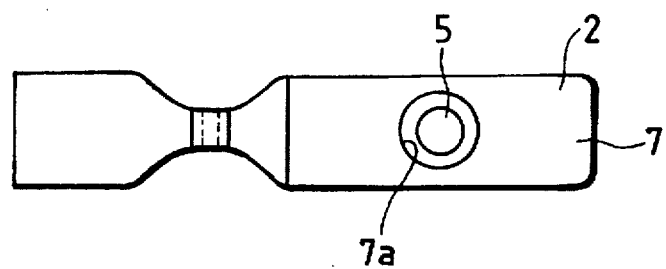
FIG. 3 is a plan view showing the construction of the second arm shown in FIG. 1.

FIGS. 1 to 3 illustrate the construction of a multipurpose sensor according to an embodiment of the invention. The holding member (hereunder referred to as the "gripper") of the sensor consists of a pair of arms 1 and 2 which are coupled in the middle by means of a shaft 3 in such a way that they can pivot about the shaft 3. Arm 1 has a light-emitting device 4 fitted in an end portion in a face-to-face relationship with a light-receiving device 5 that is fitted in an end portion of the other arm 2. The electrodes 6 and that are each made of an electrically conductive elastic material are bonded to those surfaces of the arms 1 and 2, respectively, which face each other. Electrode 6 (or 7) has a center hole 6a (or 7a) through which the light issuing from the light-emitting device 4 passes to fall on the light-receiving device 5. Arms 1 and 2 are pivotally urged by means of a spring (not shown) in such a direction that electrodes 6 and 7 are brought into contact with each other.

Electrodes 6 and 7 are typically made of a highly elastic polyurethane foam that has electrically conductive carbon particles bonded thereto by means of a special binder. The thickness of the electrodes is such that even if they are deformed by the compressive force that is exerted when the gripper holds a body part of interest, neither the light-emitting device 4 nor the light-receiving device 5 will contact the body part of interest or that they will not impede the blood flow in that body part in spite of their contacting the latter. The strength of the spring that pivotally urges the arms 1 and 2 is such that even if the electrodes 6 and 7 deform elastically to compress the human body of interest, they will in no way impede the blood flow in that part but can effectively prevent accidental disengagement of the sensor.

Figure 4:
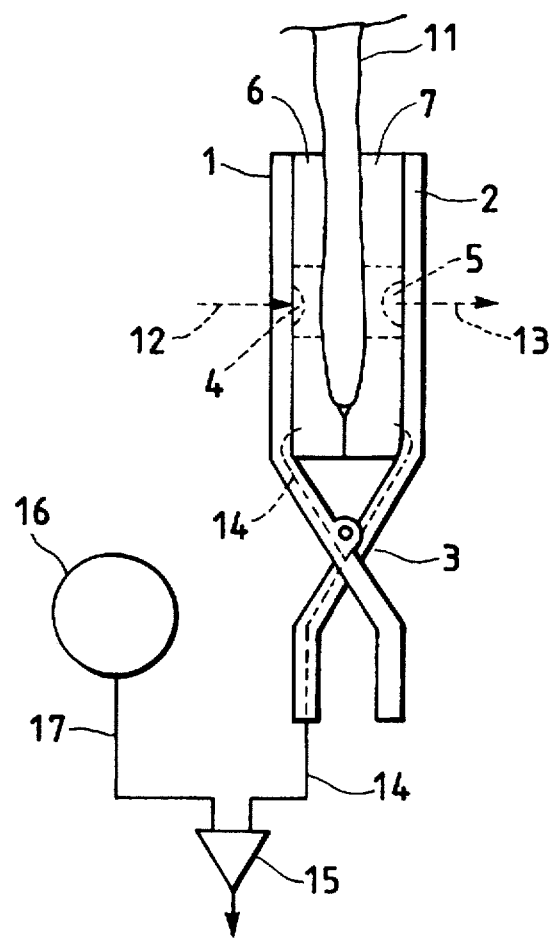
FIG. 4 is a sketch illustrating the action of the multi-purpose sensor of the embodiment.

FIG. 4 illustrates how the gripper of the multi-purpose sensor of the embodiment under consideration holds an earlobe 11 as a body part of interest for measuring the velocity of pulse wave propagation. The light-emitting device 4 is supplied with a voltage via a lead wire 12 and the light-receiving device 5 produces an electric signal as a result of photoelectric conversion of the light that has passed through the earlobe 11. The electric signal is sent to a measuring unit (not shown) via a lead wire 13. This signal serves as a pulse wave signal.

According to the embodiment under consideration, the light-emitting device 4 and the light-receiving device 5 which constitute the pulse wave detecting sensor, as well as the electrodes 6 and 7 for detecting electrocardiogram signals are provided on the gripper in such a way that the light-emitting device 4 is integral with the electrode 6 whereas the light-receiving device 5 is integral with the electrode 7. Because of this arrangement, the number of electrodes that have to be attached to the human body can be reduced by one, thereby mitigating the discomfort to the subject, the possibility of skin rash and the feeling of constraint that will be perceived by the subject. In addition, the sensor can be attached or detached from the body easily enough to reduce the overall cost in use. As a further advantage, the electrodes 6 and 7 which are made of an electrically conductive elastic material ensure that the gripper will keep providing a constant holding force without impeding the blood flow through peripheral vessels. What is more, any vibrations due to body movements and other effects are absorbed to assure consistent measurement while preventing the sensor from being disengaged accidentally from the body.

The foregoing description of the embodiment concerns the case where the gripper is attached to the earlobe 11 but it should of course be understood that it may be attached to other peripheral sites of the subject's body such as a finger. Attachment to the earlobe 11, however, has the advantage that the sensor can be easily attached and that it is sufficiently insensitive to body movements to insure consistent measurement. It should also be noted that both electrodes 6 and 7 may be provided on either one of the arms of the gripper; however, if the electrodes are provided on both arms, the areas of contact with the skin of a body part is sufficiently increased to assure consistent detection of electrocardiogram signals. As for the material of electrodes 6 and 7, they need not always be made of a polyurethane foam but may be made of any other electrically conductive elastic materials.

As described on the foregoing pages, the multi-purpose sensor of the invention is characterized in that the sensing element for detecting pulse wave signals and the electrodes for detecting electrocardiogram signals are provided to form an integral assembly with the holding member, so the number of detecting members that have to be attached to the subject can be reduced to mitigate the discomfort which he may feel during measurement. If the electrodes are made of an electrically conductive elastic material, the blockage of the blood flow in the site of sensor attachment to the subject can be effectively prevented without increasing the chance of its accidental disengagement from the body, thereby assuring consistent measurement of the velocity of pulse wave propagation.

What is claimed is:

1. A multi-purpose sensor comprising:

a pair of holding members for holding an object;

a light-emitting device and a light-receiving device for measuring pulse wave detection, the light-emitting device and the light-receiving device being provided within the holding members in a face-to-face relationship; and electrodes for measuring electrocardiogram, wherein said electrodes are arranged on at least one of said holding members;

wherein said electrodes are electrically connected together to obtain equal potential for measuring the electrocardiogram.

2. The multi-purpose sensor as claimed in claim 1, wherein the light-emitting device and the light receiving device are provided at an end portion of the holding members, respectively.

3. A multi-purpose sensor comprising:

a pair of holding members for holding an object;

light-emitting device and a light-receiving device for measuring pulse wave detection, the light-emitting[] device and the light-receiving device being provided within the holding members in face-to-face relationship and electrodes for measuring electrocardiogram, wherein said electrodes are arranged on at least one of said holding members;

wherein the electrodes are made of an electrically conductive elastic material.

4. The multi-purpose sensor as claimed in claim 1, wherein at least one the electrodes is provided in an end portion of one of the holding members.

5. The multi-purpose sensor as claimed in claim 3, wherein said electrically conductive elastic material covers an exposed surface of said at least one of said holding members around a portion of said surface on which one of said light-emitting device and said light-receiving device is arranged, said surface adapted to be living tissue of a patient.

* * * * *